United States Patent
Francis et al.

(10) Patent No.: US 11,350,828 B2
(45) Date of Patent: Jun. 7, 2022

(54) METHOD AND AN APPARATUS FOR DETERMINING HEMODYNAMIC STATUS

(71) Applicants: Darrel Francis, Harrow (GB); Matthew Shun-Shin, London (GB); Daniel Keene, London (GB); Zachary Whinnett, Chorleywood (GB)

(72) Inventors: Darrel Francis, Harrow (GB); Matthew Shun-Shin, London (GB); Daniel Keene, London (GB); Zachary Whinnett, Chorleywood (GB)

(73) Assignee: Imperial College of Science, Technology & Medicine, London (GB)

( * ) Notice: Subject to any disclaimer, the term of this patent is extended or adjusted under 35 U.S.C. 154(b) by 0 days.

(21) Appl. No.: 16/087,505

(22) PCT Filed: Mar. 24, 2017

(86) PCT No.: PCT/GB2017/050848
§ 371 (c)(1),
(2) Date: Sep. 21, 2018

(87) PCT Pub. No.: WO2017/163088
PCT Pub. Date: Sep. 28, 2017

(65) Prior Publication Data
US 2019/0099088 A1 Apr. 4, 2019

(30) Foreign Application Priority Data
Mar. 24, 2016 (GB) ..................... 1605111

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/7203* (2013.01); *A61N 1/36514* (2013.01);
(Continued)

(58) Field of Classification Search
CPC . A61B 5/02028; A61B 5/0402; A61B 5/4836; A61B 5/7203; A61B 5/7275;
(Continued)

(56) References Cited

U.S. PATENT DOCUMENTS

| 5,139,020 A | 8/1992 | Koestner et al. |
| 5,184,614 A | 2/1993 | Collins et al. |

(Continued)

FOREIGN PATENT DOCUMENTS

| WO | WO03041587 | 5/2003 |
| WO | WO-2006008535 A1 | 1/2006 |

(Continued)

OTHER PUBLICATIONS

International Preliminary Report on Patentability of the International Searching Authority, dated Oct. 4, 2018, from International Application No. PCT/GB2017/050848, filed on Mar. 24, 2017. 10 pages.

(Continued)

*Primary Examiner* — Carl H Layno
*Assistant Examiner* — Jane C Kalinock
(74) *Attorney, Agent, or Firm* — HoustonHogle LLP

(57) ABSTRACT

A device and a method thereof for determining a hemodynamic state of an individual from a magnitude of a perfusion signal or a signal which is a measure of a volume of blood in the thoracic cavity of the individual, wherein the control device is configured to receive a first signal and a heart rate signal, divide the first signal into frames, wherein a frame length is determined from an oscillation period of the heart rate signal, and determine a magnitude of the first signal (Continued)

Haemodynamically tolerated VT caused systolic blood pressure to drop by only 24%, laser doppler oscillatory power remained above 2% from at least two frames, so as to obtain a more reliable magnitude of the first signal.

20 Claims, 7 Drawing Sheets

(51) Int. Cl.
    *A61N 1/39* (2006.01)
    *A61N 1/365* (2006.01)
    *A61N 1/37* (2006.01)
    *A61B 5/318* (2021.01)

(52) U.S. Cl.
    CPC ......... *A61N 1/3702* (2013.01); *A61N 1/3904* (2017.08); *A61N 1/3925* (2013.01); *A61N 1/3962* (2013.01); *A61B 5/318* (2021.01); *A61B 5/4836* (2013.01); *A61B 5/7275* (2013.01); *A61B 5/7282* (2013.01)

(58) Field of Classification Search
    CPC .. A61B 5/7282; A61N 1/365; A61N 1/36514; A61N 1/3702; A61N 1/3904; A61N 1/3925; A61N 1/3962
    USPC .......................................................... 600/513
    See application file for complete search history.

(56) References Cited

U.S. PATENT DOCUMENTS

| | | | |
|---|---|---|---|
| 5,188,106 | A | 2/1993 | Nappholz et al. |
| 8,483,822 | B1 * | 7/2013 | Gilman ................ A61N 1/3968 607/5 |
| 2005/0027322 | A1 | 2/2005 | Warkentin |
| 2005/0288721 | A1 | 12/2005 | Girouard et al. |
| 2007/0060785 | A1 | 3/2007 | Freeman et al. |
| 2007/0255148 | A1 | 11/2007 | Bhunia |
| 2008/0208066 | A1 * | 8/2008 | Cinbis ................ A61B 5/14542 600/504 |
| 2009/0163969 | A1 * | 6/2009 | Donofrio ............. A61B 5/1459 607/6 |
| 2010/0030086 | A1 | 2/2010 | Zielinski et al. |
| 2011/0202099 | A1 | 8/2011 | Makdissi |
| 2012/0123246 | A1 | 5/2012 | King et al. |
| 2013/0030307 | A1 * | 1/2013 | Rajan ................... A61B 5/4836 600/479 |
| 2013/0072806 | A1 | 3/2013 | Zhang |

FOREIGN PATENT DOCUMENTS

| | | |
|---|---|---|
| WO | WO2011026669 | 3/2011 |
| WO | WO-2012096878 A2 | 7/2012 |

OTHER PUBLICATIONS

"International Application Serial No. PCT/GB2017/050848, International Search Report dated Jun. 6, 2017", (Jun. 6, 2017), 6 pgs.
"International Application Serial No. PCT/GB2017/050848, Written Opinion dated Jun. 6, 2017", (Jun. 6, 2017), 8 pgs.
Search Report, dated Jun. 1, 2016, from Great Britain Application No. GB1605111.2. 4 pages.
Gilland, D.R., et al., "Simultaneous Reconstruction and Motion Estimation for Gated Cardiac ECT," IEEE Transaction on Nuclear Science, 49(5): 2344-2349 (2002).
Nabutovsky, Y., et al., "Chronic Performance of a Subcutaneous Hemodynamic Sensor," PACE, 35: 919-926 (2012).
Turcott, R.G., et al., "Hemodynamic Sensing Using Subcutaneous Photoplethysmography," Am. J. Physiol. Heart Circ. Physiol., 295: H2560-H2572 (2008).
Turcott, R.G., et al., "Identification of Hemodynamically Unstable Arrhythmias Using Subcutaneous Photoplethysmography," J. Cardiovasc. Electrophysiol., 21: 448-454 (2010).
Keene et al., "Quantification of Electromechanical Coupling to Prevent Inappropriate Implantable Cardioverter-Defibrillator Shocks," JACC: Clinical Electrophysiology, 5(6): 1-12 (2019).
Examination Report, dated Apr. 1, 2021, from Great Britain Application No. GB1605111.2. 4 pages.

* cited by examiner

METHOD AND AN APPARATUS FOR DETERMINING HEMODYNAMIC STATUS

PRIORITY APPLICATIONS

This application is a U.S. National Stage Filing under 35 U.S.C. 371 from International Application No. PCT/GB2017/050848, filed on Mar. 24, 2017, and published as WO2017/163088 on Sep. 28, 2017, which claims the benefit of priority to United Kingdom Application No. 1605111.2, filed on Mar. 24, 2016; the benefit of priority of each of which is hereby claimed herein, and which applications and publication are hereby incorporated herein by reference in their entirety.

FIELD OF THE INVENTION

The present invention relates generally to a device for determining a hemodynamic state of an individual from a magnitude of a perfusion signal, a control system comprising a device configured to output a signal to a device for hemodynamic intervention based on a hemodynamic state of an individual determined from a magnitude of a perfusion signal and methods thereof.

BACKGROUND OF THE INVENTION

Cardiac arrhythmia are a group of conditions known in the field of cardiology in which the heartbeat is irregular, too fast or too slow when compared to a normal heartbeat. Various different implantable or externally wearable devices can be used to treat more serious types of arrhythmia, which may cause the individual symptoms such as dizziness, passing out, heart failure or death. Ventricular tachycardia (VT) is a type of cardiac arrhythmia which originates from the ventricles (the main pumping chambers of the heart). In VT, the heartbeat is too fast, for example above 100 beats per minute, and this is one of the more serious types of arrhythmia. VT is often treated using an implantable cardioverter defibrillator (ICD) or externally wearable defibrillator, which delivers a therapy in a form of a rapid sequence of electrical impulses (overdrive pacing) or an electrical shock (defibrillation) to the heart, in an attempt to restore a normal rhythm in the heartbeat.

An ICD and other implantable or externally wearable devices that monitor and/or treat cardiac arrhythmia may use various physiological parameters for monitoring an individual's conditions and for managing or controlling therapies delivered to an individual. The most commonly used physiological parameter for determining the individual's cardiac condition are measurement of electrical signals originating from the ventricles in the heart (the main pumping chambers). In general, such cardiac electrical signals represent the heartbeat. Whilst cardiac electrical signals can be used as an indicator of the individual's condition, under some circumstances the information obtained from the cardiac electrical signal may not be sufficient to determine the individual's condition and hence make a decision on whether a therapy should be delivered by the implantable or externally wearable device or not.

For example, in some cases, the individual's condition may not even be reflected in the cardiac electrical signal. An example of such case is illustrated in FIGS. 1A and 1B. The two figures illustrate example signals received from an individual who suffers from VT. As mentioned above, VT is a type of tachycardia, which causes improper electrical activity of the heart and hence abnormal heart rhythm, often causing a rapid heartbeat. As noted above, the implantable device relevant to VT is an ICD, which delivers a therapy in a form of a rapid sequence of electrical impulses or an electrical shock to the heart, in an attempt to restore a normal rhythm. Externally wearable defibrillators may also be used. In some cases, VT may be well tolerated so that it does not actually require a therapy to be delivered. In the case of a well-tolerated VT, it is highly preferable to delay or even omit the delivery of a therapy, as an unnecessary therapy can be harmful and/or uncomfortable. For example, sometimes the rapid sequence of electrical impulses (overdrive pacing) can cause VT to deteriorate into a worse form of VT. As another example, electric shocks (defibrillation) are uncomfortable and may even worsen the long-term function of the heart causing an increased probability of death in the long term. However, it is difficult to distinguish such well tolerated VT from an electrocardiogram (ECG) signal, which is a cardio electrical signal, alone. As yet another example, an ICD lead which is configured to sense the electrical signal of the heart may be damaged, for example due to fracture. This may cause noise to be included in the sensed electrical signal, and such noise can be incorrectly interpreted as an arrhythmia (VT or Ventricular Fibrillation (VF)).

In both FIGS. 1A and 1B, the data collected during sinus rhythm illustrate data collected where the heart of the individual is working normally, and the data collected during simulated VT illustrate data collected during VT. The horizontal axis represents time. For FIG. 1A, VT occurs around 00:22, and for FIG. 1B, VT occurs around 00:27. Looking at the ECG signal, it is clear when VT occurs in both cases. The ECG signals in FIGS. 1A and 1B are not significantly different and an ICD relying solely on the ECG signal would determine that the individual requires a therapy to be delivered in both cases of FIG. 1A and FIG. 1B, in view of the increased heart rate that falls within a predetermined abnormal range. Studying the relevant blood pressure signal (BP signal), which indicates the hemodynamic state of the individual; a different conclusion regarding the delivery of a therapy can be reached. In the case of FIG. 1A, it can be seen that the blood pressure does not fall significantly even after VT start at 00:20. This indicates a well-tolerated VT which is defined as VT which is associated with preserved cardiac output. As can be seen by the drop in the blood pressure, cardiac output may decline compared to normal sinus rhythm but is sufficient to ensure that perfusion to the brain and other major organs is preserved. Individuals under well tolerated VT therefore do not feel dizzy or lose consciousness. In contrast, the BP signal in FIG. 1B drops significantly when VT occurs, which indicates that this VT is not well tolerated and there is not enough cardiac output to ensure that perfusion to the essential major organs are being achieved. As such, a delivery of a therapy is necessary in the case illustrated in FIG. 1B.

Unfortunately, BP signals are not readily available to implantable or externally wearable devices for constant monitoring. In the place of BP signals, it has been found that tissue perfusion signals can also indicate hemodynamic state of an individual, much like a BP signal. A tissue perfusion signal can be acquired by a number of different methods including laser Doppler, spectroscopy and ultrasound Doppler. As an example, tissue perfusion signals obtained using a laser Doppler method are illustrated in FIG. 1A and FIG. 1B. As can be seen in FIG. 1A, the perfusion signal also maintains some perfusion level, even if lower than in a normal sinus rhythm, during a well-tolerated VT. As illustrated in FIG. 1B, perfusion signal also decreases dramatically during VT which is not well tolerated. Therefore, perfusion signal can be used as a useful indicator to determine the individual's condition for use in deciding whether a therapy needs to be delivered or not.

An example of an ICD system including a tissue perfusion sensor module is disclosed in US 2013/0030307 A1. Here, both the ECG signal and the perfusion signal measurement are used to determine whether a therapy should be delivered or not. The problem with such a system is that signals derived from local perfusion data are labile in the presence of the individual's movement, position, placement of the sensor, orientation either within the body or, if externally positioned, the position of the sensor externally. In particular, if the individual collapses and then twitches (a common occurrence upon fainting) or is shaken by another person, then this motion can generate an artificial fluctuation in the tissue perfusion signal whose frequency may lie in the range of frequencies that might be expected from genuine beating of the heart and therefore may be difficult to distinguish from genuine beating of the heart. The possibility of this makes the tissue perfusion signal, on its own, an unreliable indicator of whether the patient is genuinely having perfusion of the organs. As such, regardless of the method used to obtain tissue perfusion signal, currently known methods of sensing and processing of the tissue perfusion signals are prone to being affected by relatively large artificial ("noise") components hence limiting the reliability and clinical utility of using hemodynamic status derived from the processed perfusion signal. This will be illustrated later with examples.

As such, the device according to the present invention processes the perfusion data to produce a signal which is not prone to being affected by high noise components of the signal and hence derives hemodynamic status of the individual in a reliable manner. Whilst an ICD device is mentioned as an example application of the present invention, it will be appreciated by the skilled reader that a reliable detection of a hemodynamic state would be useful for many other implantable or externally wearable devices such as pacemakers or nerve stimulators, and hence the present invention may be used in conjunction with various different implantable or externally wearable devices including an ICD device.

The present invention seeks to provide a method and an apparatus which is able to determine the individual's condition more reliably for monitoring the individual's condition and for guiding therapy delivery by an implantable or externally wearable device. The present invention further seeks to address, overcome or mitigate at least one or other disadvantages associated with the previously-known method and apparatus for determining the individual's condition to determine whether a therapy should be delivered by an implantable or externally wearable device or not.

SUMMARY OF THE INVENTION

According to an aspect of the present invention there is provided a device for determining a hemodynamic state of an individual from a magnitude of a first signal, wherein the first signal is a perfusion signal or a signal which is a measure of a volume of blood in the thoracic cavity of the individual, wherein the device is configured to: receive the first signal and a signal representative of the heart rate from the individual; divide the first signal into frames, wherein a frame length is determined from an oscillation period of the heart rate signal; and determine a magnitude of the first signal from at least two frames.

A signal which is a measure of the volume of blood in the thoracic cavity may be a lead impedance signal for example.

Hemodynamic state describes whether the perfusion of a relevant body part (e.g. an organ) of an individual is adequate or not. It is a continuum with many possible levels between very good hemodynamic and very poor hemodynamic. In the present invention, the hemodynamic state is indicated as a value, wherein this value corresponds to a magnitude of a perfusion signal. This hemodynamic state, which is a variable value, may be compared against predetermined threshold values or other indicative marker values to determine whether the perfusion at the relevant body part is adequate or not. A series of hemodynamic state values may be determined continuously. This may also happen in real time as the perfusion signal is being acquired, or over a period of time for a perfusion signal which has already been acquired.

An indication of the hemodynamic state of the individual can also be indicated as a measure of the volume of blood in the thoracic cavity.

In an embodiment, the first signal is a perfusion signal. The heart rate signal may carry electrocardiogram data of the individual. The frame length may be determined solely in a time domain. The signal being processed solely in a time domain minimises the processing power requirement of the control device. The divided perfusion signal oscillates in synchrony with an oscillation of a heartbeat derivable from the heart rate signal. The segmented perfusion signal does not necessarily oscillate in the same phase, and may oscillate with a phase shift from the oscillation of the heartbeat. Each perfusion signal frame may oscillate in synchrony with an oscillation of a heart beat corresponding to the specific perfusion signal frame. The oscillation period may be intervals between successive cardiac cycles such as R wave-to-R wave intervals. R waves may be the easiest to detect. Any other fiducial marker may be used. The device may be further configured to perform a correction of any mismatch between the phase of the perfusion signal and the phase of the heart rate signal.

The device may be configured to combine at least two frames of the divided perfusion signal.

At least two segments of perfusions signals corresponding to perfusion signal of at least two frames may be combined according to the coherency of the frame. The multiple perfusion signal frames may be combined by being summated first. The multiple perfusion signal frames may be combined by being averaged. The multiple frames of perfusion signals may be combined by many different methods including the mean, median or Winsorized mean.

The device may find the magnitude of the perfusion signal as an amplitude of the combined perfusion signal. This may include the amplitude being an absolute value, a relative value, or a function thereof.

The amplitude of the summated signal may be found using various methods including the range of the data, standard deviation, or interquartile range.

Using the relationship between heart beat signal and the perfusion signal, general position of the relevant peak and trough can be predicted. By basing the frame length on an oscillation period of the heart rate signal, a single trough and a single peak corresponding to a single heartbeat are expected to be in a single frame. Such peak and trough caused by a heartbeat in each frame correspond in position on a time scale. Any noise in the signal or any peak or trough that are merely noise may be discounted as a result of the summation of the divided perfusion signal, as the peak and the trough that have been caused by the heart beat will correspond in time in every frame. The frames may be standardised. In other words, where the frame length vary due to any variation in heart rate, before summation the frames are adjusted such that the frame lengths are the same for all the frames.

The device may be configured to standardize the perfusion signal prior to combining at least two frames of the perfusion signal.

The perfusion signal frames may be standardized using one of many methods including subtraction of the mean, or performing a linear regression and subtracting the result of this.

The device may be configured to standardize the perfusion signal prior to combining at least two frames of the perfusion signal.

In the device, the frame length may be determined from an average oscillation period of the heart rate signal.

The heart rate signal acquired over a certain period of time may be used for calculating an average oscillation period. In other embodiments, the frame length may vary from segment to segment. In this case, the frame length may be determined from the corresponding specific R-R interval of an associated heart rate signal. The frames of the perfusion signal can then be modified so that they are all of the same length before summation. Frames of the perfusion signal which are determined to deviate substantially in length may not be included in the summation, for example, frames which deviate in length by more than 100 ms from a benchmark length may be excluded, or frames which deviate in length by more than 25% from a benchmark length may be excluded.

The device may be configured to output a confidence measure value which indicates the similarity of the divided perfusion signals in different frames that have been combined.

Such similarity among the segmented perfusion signals that have been summated may be found using correlation coefficient, standard deviation from the mean of the summated signal, or concordance of the sign of the signal after subtraction of the mean. Many other methods known to the skilled person may be used.

The device may be configured to receive a multiple number of perfusion signals and determine a magnitude of each perfusion signal from at least two frames of the same perfusion signal.

In some cases, perfusion signals from a number of sensors may be received by the device. The plurality of sensors may be placed in or on different parts of the patient and hence be configured to obtain perfusion signals from different parts of the patient. In other cases, the plurality of sensors may be closely located, for example in a single device, but be pointing in different directions. A device having a plurality of sensors can be robust against any false or low quality perfusion signal that may be received. This is because there is lower chance of both sensors being faulty or collecting low quality, such that even if one of the sensors is not providing a high quality signal, the device can rely on the other sensor for high quality signal. The device may even compare the two signals to indicate whether one of the sensors seem to be faulty or should be re-positioned. In any case, where a plurality of perfusion signals are received from a plurality of sensors, the signal from each sensor is processed as described above. This is to say, each signal is divided into frames, wherein a frame length is determined from an oscillation period of the heart rate signal, and at least two frames of the same signal are combined to derive a magnitude of each signal, wherein the magnitude represents the local hemodynamic state of the individual at the location where the sensor is located. As such, a magnitude representing a local hemodynamic state of the individual can be obtained from each signal. Each of the magnitude may be considered separately to consider the local hemodynamic state of the individual, or the magnitudes obtained from signals obtained by different sensors may be combined to obtain an average hemodynamic state of the individual. The magnitudes from different signals may be combined using various different methods collating multiple values, such as averaging them, summing them up or taking the highest and the lowest values.

The sensor may be internal or external. The sensor may be anon-implantable hemodynamic sensor (for example on a watch) which senses the perfusion signal. The sensor may communicate remotely with the device. The sensor may be an externally wearable sensor.

The device itself may also be an externally wearable device, for example part of a watch. The device may comprise one or more sensors. The device may comprise a sensor to detect and generate a perfusion signal and/or a sensor to detect the heart rate from the individual. The device may comprise a non-implantable hemodynamic sensor.

The device may be configured to associate the perfusion signals with concurrently received heart rate signal.

The device may be configured to receive a plurality of heart rate signals from different sensors or leads, for example, atrial, left ventricular or electrodes implanted in the generator header. As mentioned above, damaged electrical sensors or ICD or external defibrillator leads can result in inappropriate shocks being delivered, due to the noise in the sensed signal being interpreted as VT or VF. In order to avoid this problem, the device may be configured to request for a different heart rate signal. In some embodiments, this is requested periodically to check if the electrical sensor or the ICD or external defibrillator lead are functioning correctly, or once the device determines that VF or VT is detected. For example, there may be present at least two of a left ventricular lead, a right ventricular lead, a left atrial lead and a right atrial lead. For example, where the device initially uses the heart rate signal from the left ventricular lead and determines that VF or VT is detected, it may request for heart rate signal from one of the atrial leads for use when dividing up the perfusion signal (i.e. to determine the frame length). If, based on the heart rate signal from the atrial lead, it is determined that the individual is in a normal rhythm, then the device determines that the ventricular lead is malfunctioning.

In other words, the device may be configured to determine the frame length for the perfusion signal based on different heart rate signals and compare the result to determine whether any of the sensors or leads obtaining the heart rate signal are faulty. The device may also be configured to disregard if the results based on the different heart rate signal indicate that there is no need for hemodynamic intervention.

In some embodiments, the device is configured to mitigate for oversensing by the heart rate sensor. This may be done by determining whether the determined magnitude of the perfusion signal deviates from a benchmark measure, if it does deviate, modifying the oscillation period of the heart rate signal used to determine the magnitude of the perfusion signal, and determining a new magnitude of the perfusion signal.

The device may comprise a controller for outputting a signal to an implantable or externally wearable device for hemodynamic intervention based on the determined hemodynamic state of an individual.

The hemodynamic intervention may treat cardiac arrhythmia.

The device may comprise a controller for outputting a signal to a device for hemodynamic intervention in response to the determined hemodynamic state of an individual. For example, the device may be configured to output a signal to control the device for hemodynamic intervention based on the determined magnitude of the perfusion signal. The device may be configured to output a signal to modify the settings of the device for hemodynamic intervention, for example, where the device for hemodynamic intervention is a pacemaker to alter the AV (atrioventricular) and/or VV (ventriculo-ventricular) delays.

According to another aspect of the present invention there is provided a control system for hemodynamic intervention comprising a device as described above and the device for hemodynamic intervention, wherein the controller is configured to output a signal to control the device for hemodynamic intervention based on the determined magnitude of the first signal.

According to another aspect of the present invention there is provided a control system for hemodynamic intervention comprising a device as described above and an implantable device, wherein the controller is configured to output a signal to activate the implantable device when a magnitude of the heart rate signal is above a first threshold value and a magnitude of the first signal is below a second threshold value.

According to another aspect of the present invention there is provided a control system for hemodynamic intervention comprising a device as described above and a device for hemodynamic intervention, wherein the controller is configured to output a signal to activate the device for hemodynamic intervention when a magnitude of the heart rate signal is above a first threshold value and a magnitude of the first signal is below a second threshold value.

In an embodiment, the first signal is a perfusion signal. Different first and second threshold values may be used depending on the location at which the perfusion signal sensor is placed on or within the body.

The device for hemodynamic intervention may be a defibrillator device. In the system, the device may be an implantable device, for example an implantable cardioverter defibrillator. The implantable device may alternatively be a pacemaker device for example a Cardiac Resynchronisation Therapy (CRT) device. The device may be an externally wearable device, for example an externally wearable defibrillator device such as a LifeVest™ device.

The device and the device for hemodynamic intervention may be integrated or separate. One or more sensors may be integrated with the device and/or the device for hemodynamic intervention.

In the system, the multiple frames of the perfusion signal may be collected over a predetermined time period. This time period may be programmable, such that the predetermined time period may be chosen or adjusted by the user. The predetermined time period may be set as the charge time of the device for hemodynamic intervention. The predetermined time period may be set to be prior to charging of the device. Monitoring during the device for hemodynamic intervention charge time may maximize the available data before a decision for therapy to be delivered. It is desirable to collect the hemodynamic information before charging, as charging drains the device battery.

According to another aspect of the invention, there is provided a method for determining a hemodynamic state of an individual from a magnitude of a first signal, wherein the first signal is a perfusion signal or a signal which is a measure of a volume of blood in the thoracic cavity, wherein the method comprises the steps of: receiving the first signal and a signal representative of the heart rate from the individual; dividing the first signal into frames, wherein a frame length is determined from an oscillation period of the heart rate signal; and determining a magnitude of the first signal from at least two frames.

In an embodiment, the first signal is a perfusion signal.

In the method, at least two frames of the divided perfusion signal may be combined.

In the method, the magnitude of the perfusion signal may be found as amplitude of the combined perfusion signal.

In the method the perfusion signal may be standardized prior to combining at least two frames of the perfusion signal.

In the method, the frame length may be determined from an average oscillation period of the heart rate signal.

In the method, a confidence measure value, which indicates the similarity of the divided perfusion signals in different frames that have been combined, may be output.

In the method, a multiple number of perfusion signals may be received and a magnitude of each perfusion signal from at least two frames of the same perfusion signal may be found.

In the method, the perfusion signal may be associated with concurrently received heart rate signal.

According to another aspect of the present invention, there is provided a control method for outputting a signal to a device for hemodynamic intervention based on a hemodynamic state of an individual determined from a magnitude of a first signal as described above.

The device may be an implantable device, for example an implantable cardioverter defibrillator or a pacemaker device. Alternatively, the device may be an externally wearable device, for example an externally wearable defibrillator device such as a "LifeVest™" device.

According to another aspect of the present invention, there is provided a computer storage medium comprising code for execution by a processor, the code, when executed by a processor causing the processor to perform the methods described above.

DETAILED DESCRIPTION

Figures 1A, 1B:
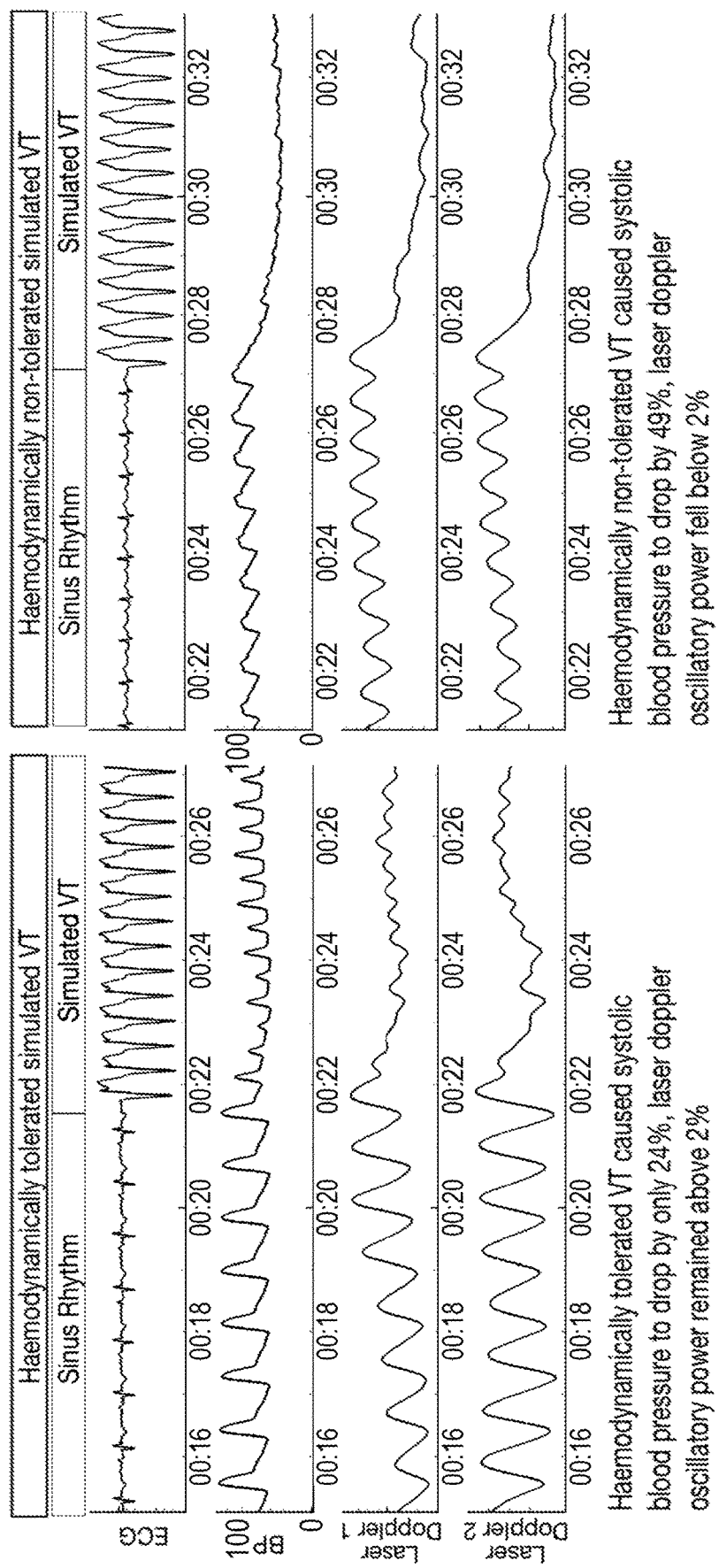
FIG. 1 is an example illustrating the information which can be represented by different physiological parameters.

Many current implantable or externally wearable devices monitor and/or deliver therapies for treating disorders of the cardiac rhythm based on electrical information obtained from the electrical changes that are sensed from the heart. Such electrical activity of the heart represents the heartbeat, but relying solely on this information may not be sufficient to guide therapy reliably as mentioned above.

Any misguidance of therapy can be particularly harmful where the device is an implantable or externally wearable cardiac defibrillator device which delivers therapy for treating cardiac arrhythmias, because it involves delivering a rapid sequence of electrical stimuli (overdrive pacing) or larger electric shocks (defibrillation) to the heart in an attempt to restore the heart to a normal rhythm. Overdrive pacing can be harmful because sometimes it causes the tachycardia to deteriorate into a faster tachycardia which can worsen the function of the heart. Electric shocks can be extremely painful to the individual if delivered while the individual is conscious. Whilst the present invention would be advantageous when used with the application of any of the mentioned implantable or externally wearable devices, it is particularly useful when used in combination with an implantable or externally wearable defibrillator device, as delivering such high level shock to the heart due to misguidance of the data received is more detrimental than if a lower level impulses are applied as a result of a misguidance.

In the case where the implantable or externally wearable device is an ICD, for example, electrical noise from a damaged lead or sensor maybe indistinguishable from the electrical signal of a pathological rhythm such as ventricular fibrillation (VF). The ICD lead or sensor may be damaged from, for example, a fracture. Such noise cause by the damaged ICD lead or sensor may be incorrectly interpreted as an arrhythmia and the device may inappropriately deliver a therapy that is harmful in this situation. In the case where the device is an externally wearable defibrillator, similar problems with noise causing inappropriate shocks can occur. Similarly, the tolerability of various tachy-disrhythmias varies between individuals. It is advantageous to guide therapy delivery using the patient's hemodynamic status during these real or presumed dysrhythmias, as the hemodynamic information can be used to prevent shocks being delivered in the absence of an arrhythmia. In response to the detection of an apparent arrhythmia, the hemodynamic state of the individual is determined, again, with an alternative signal representative of the heart rate. If this determines that no intervention is required, then it is an indication that the lead or sensor is damaged. Devices implanted to prevent vasovagal syncope may also benefit from having a hemodynamic signal to guide treatment.

In addition, the use of hemodynamic state in conjunction with the heart rate signal may be advantageous in that there may be situations wherein it is difficult to distinguish whether a therapy should be delivered or not. For example, there may be a case where heart rate increases for reasons that are not a tachyarrhythmia that requires therapy. A common example is when a patient is engaged in physical activity and the heart rate increases through the normal control systems of the body.

In tachyarrhythmias requiring treatment, the electrical activations of the heart are generally activating the muscle cells of the various regions of the heart occur in an abnormal sequence, which causes the effectiveness of the heart as a pump to be lower than it otherwise would be, even at the same heart rate. Therefore, it is important to be able to distinguish between the situation of the heart rate increasing through normal processes, where the pumping efficiency of the heart is better, versus, the situation of the heart rate increasing through abnormal processes (ventricular tachycardia), where the pumping efficiency of the heart is worse. This distinction cannot be accurately made solely on the heart rate.

As such, guidance as to whether a therapy should be delivered to the heart only based on heart rate is not reliable. As it is nevertheless true that cardiac electrical signals provide useful information, the cardio electrical signal may be used in combination with the perfusion signal to determine whether or not a therapy should be delivered.

As previously mentioned, known methods of quantifying the perfusion data rely on an assessment of an absolute magnitude of the signal which is subjected to positional and noise components. Firstly, it is very difficult to predict the exact positions of the peak and the trough of the perfusion signal that have been caused by the heart. Secondly, even if an assumption were to be made as to where the peak and the trough of the perfusion signal may be, a measurement of an absolute magnitude of the signal at the relevant points may not reflect the actual hemodynamic state, as noise components may be included in the perfusion signal at the relevant position. Such a high noise component which is resent in a perfusion signal results in low reliability and hence clinical utility of using the perfusion signal as a factor to consider when deciding whether or not a therapy should be delivered by the device.

Figure 2:
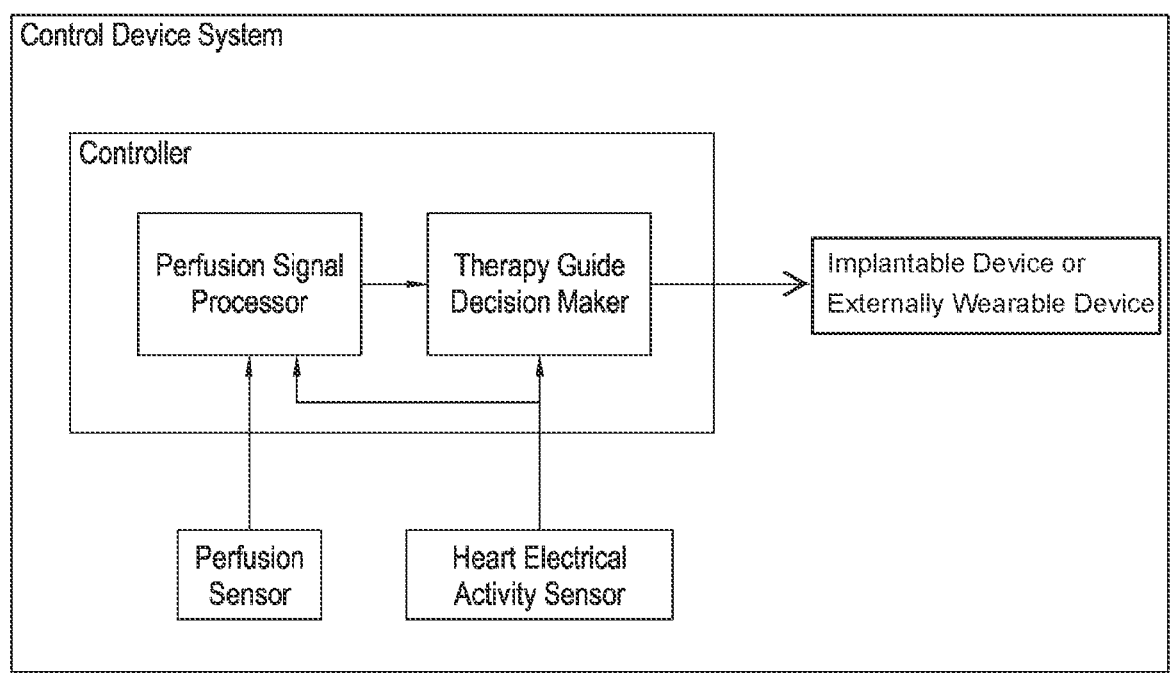
FIG. 2 is a function block diagram of a control device system according to an embodiment of the present invention.

Referring to FIG. 2, an embodiment of a control device system according to the present invention is shown. The control device system comprises a controller connected to an implantable or externally wearable device, a perfusion sensor and a heart electrical activity sensor, wherein the controller is configured to activate the implantable or externally wearable device according to the perfusion signal and the heart electrical activity signal received from the respective sensors. For example, in this embodiment, the implantable or externally wearable device is an ICD, the perfusion sensor is a laser Doppler, and the heart electrical activity sensor is an ICD lead connected to ICD. As the skilled reader will appreciate, it is not essential to measure heart activity directly. Any signal that has the same wavelength as the heartbeat may be used. The control device system may be integrated into a single implantable or externally wearable device (e.g. including the controller and one or more sensors), or only parts of the system may be integrated in the implantable or externally wearable device. For example, the controller and the implantable or externally wearable device may be integrated and the sensors may be separate devices that may not even be implanted but obtain perfusion signal and the heart electrical activity signal externally. As such, the controller, the sensors and the implantable or externally wearable device may be electrically connected to each other or be wirelessly connected. The controller may be an external device, for example an externally wearable device, which may also be integrated with one or more sensors.

The controller comprises a perfusion signal processor and a therapy guide decision maker. The perfusion signal processor is configured to receive the perfusion signal obtained by the perfusion sensor, process the perfusion signal to quantify the signal and output a hemodynamic state value representative of a hemodynamic state of the individual to the therapy guide decision maker. For example, this hemodynamic state value could be between zero and one hundred, wherein zero represents no fluctuation (and no perfusion) in the hemodynamic state and a hundred represents a very large fluctuation (high perfusion level). The therapy guide decision maker is configured to receive the heart electrical activity signal which represents heart rate of the individual and the hemodynamic state value from the perfusion signal processor and make a decision based on the information received as to whether to output a signal for activating the implantable or externally wearable device or not.

The implantable or externally wearable device may be an implantable cardioverter defibrillator (ICD), an externally wearable defibrillator, a pacemaker or a nerve stimulator. The pacemaker may be a CRT device, which is a type of pacemaker having an extra lead to pace not only the right, but also the left ventricle. A CRT device may be used for patients with heart failure for example.

An example of an externally wearable defibrillator is a LifeVest™ device. An externally wearable defibrillator may comprise two or more pads which, when the device is worn, contact the skin at appropriate locations on the chest area, each pad comprising an electrode. It may also comprise a small battery pack, which may be worn separately but connected to the pads, for example on a belt. It may also comprise a perfusion sensor and/or a heart electrical activity sensor and/or the controller. The hemodynamic sensor or perfusion signal sensor (for example laser Doppler sensor) may thus also be wearable and integrated with the externally wearable device; or may be wearable and not integrated for example as a watch or skin patch) and communicate with wired or wireless communication; or may be implanted (whilst the defibrillator is externally wearable) and communicate wirelessly to the externally wearable device. Such devices may be worn by people at risk of cardiac death who are waiting for an implantable device for example. In externally wearable defibrillator devices, similar problems as described above, where noise can cause inappropriate shocks, can occur.

The system may thus comprise any combination of an implantable or externally wearable device for hemodynamic intervention, together with an integrated or non-integrated and implantable or externally wearable perfusion signal sensor, an integrated or non-integrated and implantable or externally wearable heart rate signal sensor, and an integrated or non-integrated and implantable or externally wearable control device.

Whilst any implantable or externally wearable device would benefit from incorporating hemodynamic status determined from the perfusion signal processor of the present invention, the benefit may be particularly significant in the case where the implantable or externally wearable device is a defibrillator, as discussed above.

The perfusion sensor and the heart electrical activity sensor are configured to receive tissue perfusion signal and heart electrical activity signal from an individual. The perfusion sensor can use a variety of methods to obtain tissue perfusion signals, such as laser Doppler, spectroscopy and ultrasound Doppler. The heart electrical activity sensor obtains signals that represent the individual's heartbeat.

As explained above, the problem with previously-known implantable or externally wearable devices which sense and process tissue perfusion signals is that they are prone to being affected by high noise components hence limiting their reliability and clinical utility. In order to overcome the problem, the perfusion signal processor according to the present invention isolates the amplitude of cyclical oscillations in tissue perfusion that correspond to the cyclical electrical activation of the heart, by processing the perfusion signal based on the electrical activation oscillation period. With reference to FIG. 1A, it can be seen that the perfusion signal pulsates in synchrony (even if there is a delay or a shift) with a single heartbeat. This relationship between an oscillation period of the perfusion signal and an oscillation period of the cardiac electrical signal is used to process the perfusion signal solely in a time domain.

In essence, the perfusion signal is divided up into frames that have their length based on the oscillation period of the cardiac electrical signal. Then, at least two of the perfusion signal frames are overlapped in the sense that an average signal is outputted from the at least two perfusion signal frames. The basic principle behind this is that as the perfusion signal pulsates in accordance with the heartbeat, which is represented by the oscillation period of the cardiac electrical signal, the parts of the signal that are pulsating according to the heartbeat are averaged and any parts of the signal that are simply noise and hence not pulsating are destructively combined such that any noise components are naturally disregarded. Therefore, an amplitude of the combined perfusion signal frames is considered to be a reliable representation of the hemodynamic state of the individual. This process is illustrated as a flow diagram of FIG. 3, and described in more detail with reference to FIG. 4 below.

The perfusion signal processor is configured to process the perfusion signal received according to the following steps, which are described with reference to FIGS. 3 and 4. FIG. 4 is a schematic illustration of the perfusion signal processing steps as described in the flow diagram of FIG. 3. The flow diagram of FIG. 3 starts with step 301 of receiving a perfusion signal and a heart rate signal. Note that a cardiac electrical signal such as an ECG signal is considered to represent the heart rate of the individual, and the three terms may be used interchangeably. As can be seen in FIG. 4, stages 1.1 and 1.2, ECG signal and raw perfusion signal are made available to the control device according to this embodiment of the present invention. The sampling frequency of the perfusion data should be at least double the cardiac cycle and preferably will exceed this. For example, at a typical heart rate of 120 beat per minute, the sampling frequency should exceed at least 4 Hz. A sampling rate of up to around 100 Hz or even higher (if memory allows) may be used. The minimum sampling frequency is related to the fact that the present invention utilises the relationship between the cyclical electrical activity in the heart and the resultant oscillations in the tissue perfusion signal. If the tissue perfusion signal is sampled at less than double the frequency of the oscillations, interpretation becomes ambiguous. Therefore, the minimum sampling rate is dictated according to the Nyquist theorem.

Figure 3:
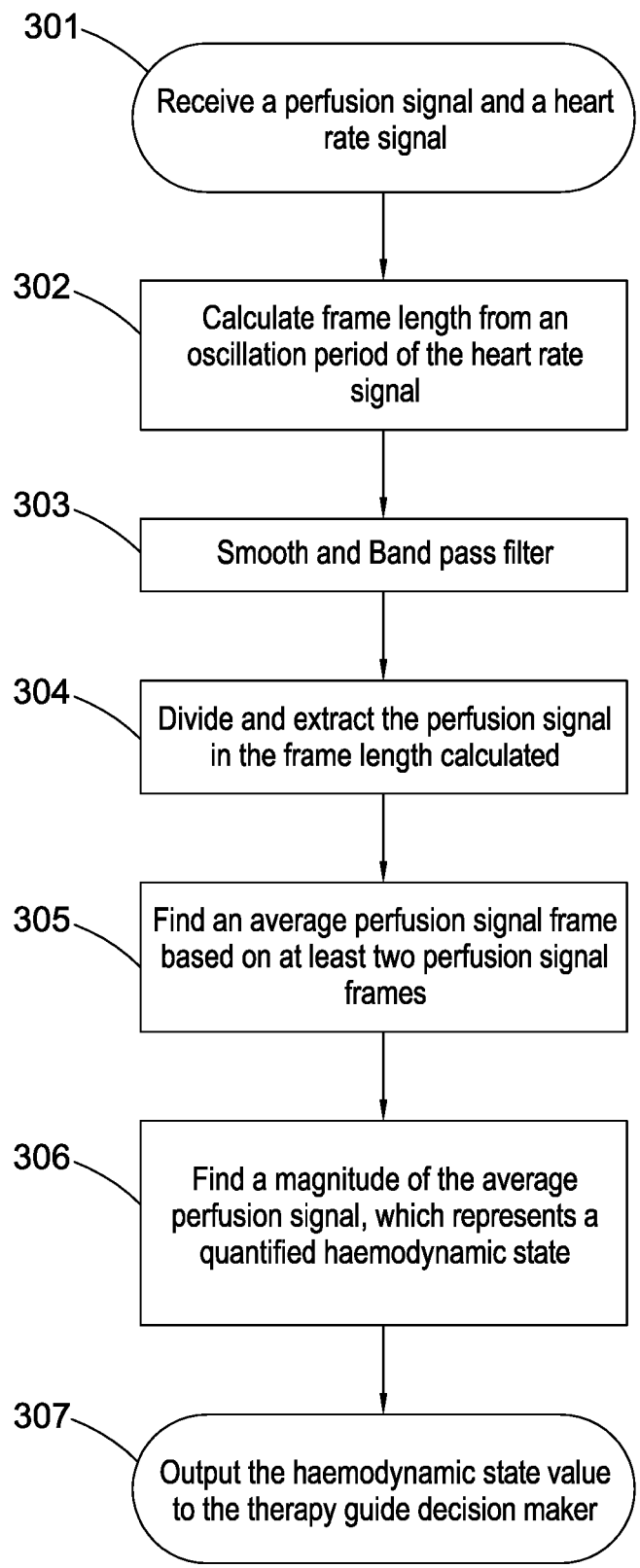
FIG. 3 is a flow diagram illustrating the perfusion signal processing steps according to an embodiment of the present invention.
Figure 4:
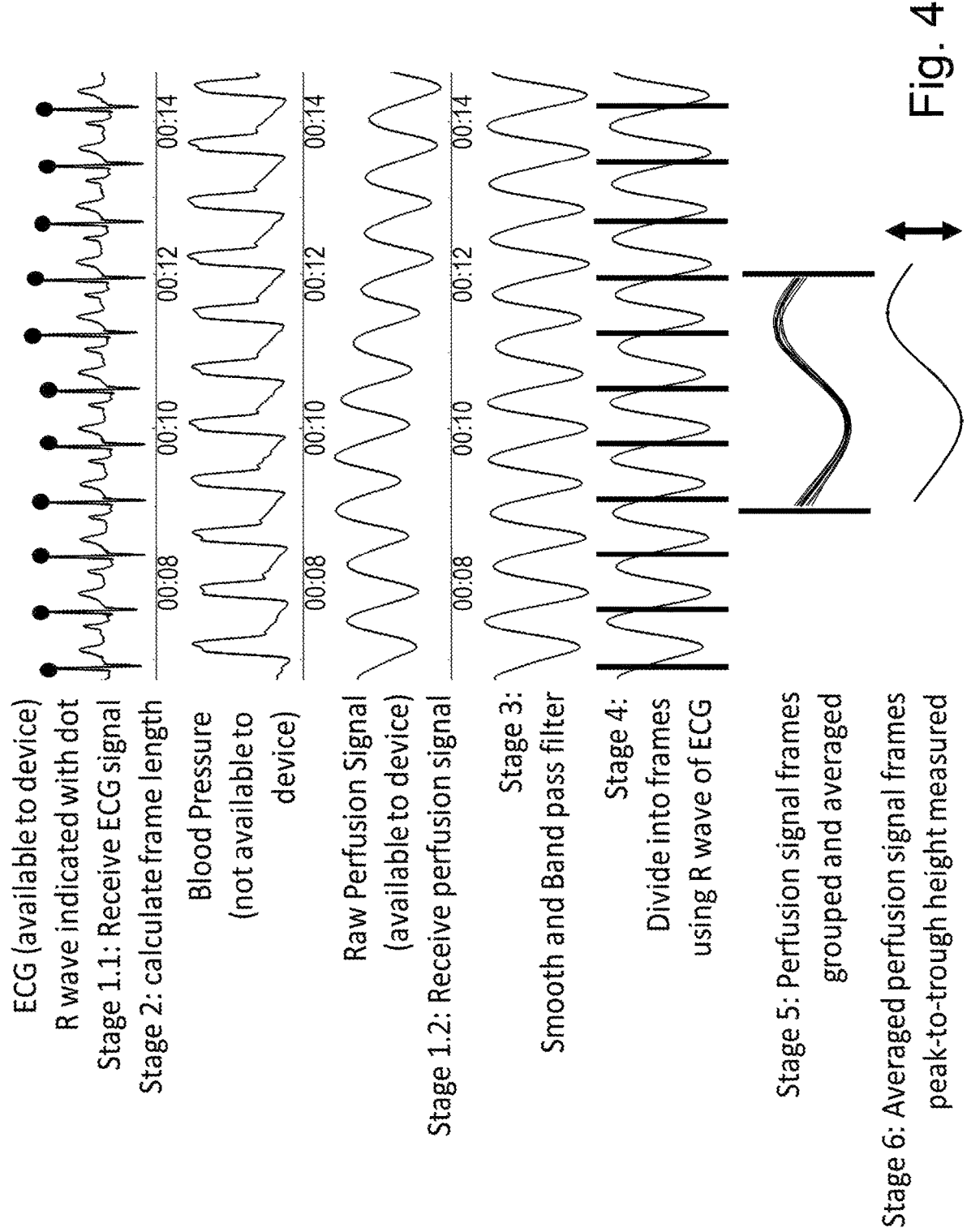
FIG. 4 is a schematic illustration of the perfusion signal processing steps according to an embodiment of the present invention.

The next step of the flow diagram of FIG. 3, step 302, is to calculate frame length from an oscillation period of the heart rate signal. This is illustrated in FIG. 4 as stage 2, wherein the R waves in the ECG signal have been marked with a dot. In this embodiment, the R waves are used to mark the interval between successive cardiac cycles (i.e. R-R interval in this case) to determine the frame length of the perfusion signal. In other words, a frame length is calculated as the time period between a detected R wave and a successively detected R wave, which is essentially an R-R interval. Therefore, a perfusion signal frame is a segment of the perfusion signal which has been extracted from the original perfusion signal over a time period equivalent to the frame length. To the skilled reader, it is evident that the electrical signal could be acquired from a lead in the atrium of the heart, rather than the ventricle of the heart. When a lead is in the atrium, the signal corresponds to the timing of atrial activation which on the 12-lead ECG is described as the P wave. The skilled reader will see that these timing signals, which are essentially the P-P interval, can be used in the same way as those of the R-R interval. Therefore, in this disclosure, the terms R wave and R-R interval should be understood to also cover the possibility of the P wave and P-P interval.

In other embodiments, the frame length may be determined based on the R-R interval of the particular heartbeat, obtained from an electrical signal from the atrial lead, which is simultaneous with the perfusion signal frame (or the perfusion signal frame portion of the perfusion signal) and therefore vary throughout the analysis period. This may be done in the case of Atrial Fibrillation (AF) or patients with frequent Ectopic beats for example. In this case, the resultant perfusion signal frames are resampled to a standardised frame length. In other words, since each perfusion signal frame length may vary, the perfusion signal frames are adjusted to have a single frame length. Thus if different frame lengths are possible, the frames of the perfusion signal can be modified before summation so that they are all of the same length. This may be done by stretching or by interpolation for example.

Optionally, frames of the perfusion signal which deviate in length significantly from a benchmark may be excluded from the summation. Thus, the device may be configured to perform a step of determining whether the frame length deviates before the summation, and if it is found to deviate, excluding the frame from the summation. For example, all frames for which the length deviates by greater than a threshold amount from the benchmark may be excluded. For example, all frames which deviate from the benchmark RR interval by an amount greater than or equal to 25% of the benchmark interval may be excluded, or all frames which deviate by more than 100 ms. The benchmark may be a mean, median or modal length for example. Alternatively, the exclusion may be performed by reference to the standard deviation or other measures. Thus during AF or any condition for which there is an irregular heart rate rhythm, the device may determine the exclusion of particularly short or particularly long R-R intervals, this being determined with reference to the mean or standard deviation or other measures.

In yet another embodiment, an average R-R interval length may be found over several heartbeats and used as the frame length.

It should be noted that any other fiducial marker and its associated interval (which is the length between successive detection of the chosen fiducial marker) may be used to define the frame length. It is often preferable to use the R waves, as they are the most predominant in an ECG signal.

In some embodiments, the perfusion signal may be smoothed using various methods, prior to dividing the perfusion signal up into frames. Such smoothing techniques include using an algorithm such as band pass filter or Savitzky-Golay filters. Such filters may remove high frequency noise such as those associated with electrical noise or muscle activity and low frequency oscillations such as those associated with respiratory activity. Oscillations within the physiological and pathological heart rates (typically between 0.5 Hz to 5 Hz) should not be filtered out. Such a step of filtering is illustrated as step 303 in the flow diagram of FIG. 3, and as stage 3 in FIG. 4 shows as stage 3, wherein the perfusion signal is smoothed using a band pass filter.

The next step, step 304, of the flow diagram in FIG. 3 is to divide and extract the perfusion signal in the frame length derived from the ECG signal. In essence, the perfusion signal is divided up into a frame of the length calculated from an oscillation cycle of the ECG signal. In this way, a peak and a trough that has been caused by a heartbeat, which is represented by the oscillation period of the cardiac electrical signal, will be contained in this frame. This is because there is a direct relationship between the oscillation period of the ECG signal and the perfusion signal. In this embodiment, the oscillation period is the same for the ECG signal and the perfusion signal. This can be seen from the ECG signal and the perfusion signal illustrated in FIG. 4, wherein the perfusion signal pulsates with the same period of oscillation as the ECG signal (in some cases there may be a delay or a shift). As such, dividing the perfusion signal up by the oscillation period of the ECG signal ensures that a single pulse comprising a peak and a trough that have been caused by the cardiac activity (and not noise) is included in each perfusion frame.

In the embodiment illustrated in stage 4 of FIG. 4, the perfusion signal frame starts at the time corresponding to the R-R interval. Stage 4 of FIG. 4 depicts the perfusion signal being divided up with the vertical lines that have been applied to the perfusion signal, wherein each vertical line corresponds with an R wave of the ECG in position on the horizontal axis, which represents time. Each pair of consecutive vertical lines may be considered to define a window which is applied to the perfusion signal to divide it up into perfusion signal frames. Here, it can be seen that the perfusion signal frame starts at the same position as the R-R interval as shown in the ECG signal.

In other embodiments, the windows may be applied slightly shifted in time, so as to account for the delay between the electrical activation of the heart and associated contraction and the corresponding increase in the tissue perfusion signal. Typically, the ECG signal and the perfusion signal are simultaneously acquired. However, there is a delay, or a slight shift, in the oscillatory cycle between the ECG signal and the perfusion signal. This delay is caused by the biological process by which the electrical activation of the heart causes the heart to contract and eject blood, which builds up a reservoir of excess blood in the large arteries, that then progressively flows through the smaller vessels, which are typically the ones detected by the sensor. Such biological delay is typically much larger than any electrical or computational delay inside the sensors that provide the perfusion signal. This biological delay is generally in the order of around 300 to 700 ms. On average this can be considered as around half a cardiac cycle and hence the window may start preceding the R wave by a fraction of the cardiac cycle such as 50%. The shift value may be fixed or customised for each individual.

Advantageously, the shift value may be selected so that the position where the midpoint of the pulse in the perfusion signal caused by the activation of the heart is centred in the window (and hence centred in the perfusion signal frame). Alternatively, the shift value may be selected so that the nadir (or start of the upstroke) of the perfusion signal aligns with the start of the window. The skilled reader will understand that it may not be possible to identify the exact peak or trough that has been caused by the electrical activation of the heart, but that it is nevertheless possible to predict whereabouts such peak and trough should be based on the general relationship between the electrical activation of the heart and the perfusion signal, and hence position the window accordingly. In view of this, the window length calculated from the ECG signal may be applied to the perfusion signal shifted by a predetermined value.

A step of correcting for any mismatch between the phase of the perfusion signal and the phase of the heart rate signal may thus be performed. This may improve coherency. This correction may comprise first detecting an R wave in the heart rate signal, then finding the next nadir (i.e. minimum) in the perfusion signal after the time point corresponding to the R-wave. The minimum can be found from a smoothed perfusion signal for example. This is the first nadir after the R wave. Electrical activity (i.e. the R wave) generally occurs a few ms prior to mechanical activity in the heart, which in turn occurs a few hundred ms before the termination of the downslow of the diastolic decay of flow/pressure (i.e. lowest point before an upstroke). The time difference between the nadir in the perfusion signal and the corresponding R wave in the ECG signal is then determined. The perfusion signal is then segmented in line with the location of the R wave plus a fixed interval, the fixed interval being calculated from the delay. In other words, the beginning of each segmentation window is located at the time point on the perfusion signal corresponding to the location of the corresponding R-wave plus the fixed interval. The end-point of the segmentation window is located a length of time after the beginning location of the window, the length of time corresponding to the duration between the R-wave and the subsequent R-wave. In the above described case, the perfusion signal and the ECG signal are aligned at the "up-sloping portion" of the perfusion signal. However, alternatively they may be aligned at the peak or at other fiducial points (such as maximum slope).

Even if the window has been applied in such a way that a perfusion signal frame contains a part of the perfusion signal pulse (e.g. 40%) that is caused by a previous cardiac activity and a part of the consecutive perfusion signal pulse that is caused by the following cardiac activity, this does not have a significant effect on the final hemodynamic state value calculated. This is because each perfusion signal frame would still overall contain a single pulse with one true peak and one true trough each caused by the cardiac activity at the same positions, such that the peaks and the troughs nevertheless line up positionally when grouped and averaged.

Once perfusion signal frames are obtained, the next step is to find an average perfusion signal frame based on at least two perfusion signal frames, as described in step 305 of the flow diagram of FIG. 3. This step is illustrated as stage 5 in FIG. 4, wherein ten perfusion signal frames are grouped together and averaged. Whilst ten perfusion signal frames are used in this example, it will be appreciated that other number of perfusion signal frames may be used, as long as more than two perfusion signal frames are used. Typically, around 2 to 50 perfusion signal frames are used. More preferably, around 5 to 20 perfusion signal frames are used. The preferred method analyses 10 to 20 heart beats which translates to around 6 seconds. This time period is short enough that any drift of the signals over time would be irrelevant. A minimum of two perfusion signal frames must be used, so that the true oscillation which has been caused by the cardiac activity can be identified and any fluctuations caused by noise disregarded. Only the true fluctuations that are caused by the cardiac activity, which therefore has the same period as the oscillation of the ECG signal, line up when the perfusion signal frames are grouped together, as in stage 5 of FIG. 4.

Any fluctuations that are caused by noise are not in phase with the oscillation period of the ECG signal and hence do not line up when the perfusion signal frames are grouped together. As such, when the perfusion signal frames are grouped together and averaged, the noise that does not pulsate according to the cardiac activities combines destructively such that the noise components of the perfusion signal frames are naturally disregarded. The perfusion signal frames may be combined by using many different methods known to those skilled in the art. These methods include finding the mean, median, or Winsorised mean. Prior to combining the signals in this way, the perfusion signal frames may be standardized by any well-known methods including subtraction of the mean or performing linear regression then subtracting the result of the linear regression. As the perfusion signal has been divided into the frames according to the oscillation period of the cardiac electrical signal, the fluctuations in the perfusion signal frames that are caused by the cardiac activity match up in position (in the time domain, position meaning position in the axis representing time). Any fluctuations that are mere noise components do not match up and hence when the perfusion signal frames are combined, any noise components are naturally disregarded. The noise components can be considered as being combined in a destructive manner.

In some embodiments, the combined multiple perfusion signal frame may again be smoothed by filtering using various different methods, including band pass filter or Savitzky-Golay filter.

A magnitude of the oscillation in the combined multiple perfusion signal frame is then found, as described in step 306 of the flow diagram of FIG. 3. Such magnitude may be calculated using one of many methods known in the art, such as the range of the data, the standard deviation, or interquartile range. In the embodiment illustrated in stage 6 of FIG. 4 an amplitude of the averaged perfusion signal frames (i.e. the combined multiple perfusion signal frame) is found by detecting the peak and the trough in the combined perfusion signal frame, and measuring the amplitude. An amplitude is an example of a magnitude of the oscillation in the combined multiple perfusion signal frames. Magnitude of the oscillation in the combined multiple perfusion signal frames could also include, for example, the integrated area of the combined multiple perfusion signal frames. Such an amplitude or a magnitude found by other methods discussed above is considered to be a representation of the hemodynamic state. In other embodiments, another magnitude such as an integration of the averaged perfusion frames may be considered. Before the magnitude is found, the combined perfusion signal frames may be checked to confirm that there is a single significant peak and a single trough. Depending on the location and positioning of the hemodynamic sensor in reference to the heart, dicrotic notch (which indicates the pressure increase upon closure of the aortic valve) may be detected, such that two peaks are obtained. However, the dicrotic notch is smaller in magnitude and it can be determined whether there is a single significant peak when two peaks are detected, by comparing the magnitude of the two peaks. If more than one peak (or more than one significant peak where two peaks are detected) or more than one trough is detected, the combined perfusion signal frames are discarded, or is assumed that the perfusion level is around zero such that only noise components remain in the perfusion signal.

Such magnitude of the oscillation of the combined perfusion signal frame is considered to represent the true hemodynamic state of an individual, as the combined perfusion signal frame oscillates with the same period as the electrical cardiac cycle (even if there is a slight phase shift). This is because, as mentioned above, any peaks or troughs that were present at the frequency that does not correspond to the cardiac electrical cycle are discarded through the combining step. Furthermore, by considering the magnitude of the oscillation rather than an absolute value at a certain point, a more reliable value can be obtained. For example, the magnitude found for each perfusion signal frame may be converted into a value that is relative to the magnitude of the averaged signal, such as the mean or median, as changes in position or the volume of tissue under consideration under the same physiological conditions tend to scale up or down the signal and the amplitude of the oscillations in similar proportion. Such a value may also be calculated by considering the signal on a logarithmic scale. Therefore, any change in the absolute value of the perfusion signal which may occur due to such scaling up or down does not severely affect the overall magnitude value of the oscillation.

In some embodiments, multiple tissue perfusion signals may be obtained and used to calculate a final assessment of the hemodynamic state. For example, there may be two perfusion sensors. One may be incorporated onto the surface of an implantable device which sits under the skin. The other could be incorporated into a pacing lead which sits in the blood stream (these examples are not exclusive). If, for example the first sensor reports a low value (such as 1), and the other a high value (such as 10), then the invention could use the average of these two numbers, i.e. 5.5, as the final assessment of the hemodynamic state. In an alternative embodiment the invention could take the highest of these numbers, namely 10, as the final assessment of the hemodynamic state. As the method of the present invention quantifies the hemodynamic state from tissue perfusion by considering the association between the electrical activity of the heart and the pulsatile nature of the tissue perfusion signal, it is not readily affected by noise and the input from multiple tissue perfusion signals can be combined from simply selecting the maximum obtained.

The final step of the perfusion signal processor is to output the hemodynamic state value to the therapy guide decision maker, as in step 307 of the flow diagram of FIG. 3. In this embodiment, the perfusion signal processor continuously outputs a hemodynamic state value calculated for a predetermined analysis period. Therefore, a series of hemodynamic state values are output to the therapy guide decision maker over time. Where the hemodynamic values are output in this manner, the hemodynamic state of the person may be continuously monitored, and the ECG signal and the hemodynamic state values may be compared to check that the ECG signal, particularly when it indicates sinus rhythm, does not contain error. In other embodiments, a hemodynamic value may be output only when requested by the therapy guide decision maker.

In some embodiments, the perfusion signal processor may also output a confidence measure of the result. Such confidence measure may be calculated based on the similarity of the individual perfusion signal frames, using various different methods including correlation coefficient, standard deviation from the mean of the combined frame, concordance of the sign of the signal after subtraction of the mean and many more.

In some embodiments, the device is configured to mitigate for oversensing of the heart rate sensor. This may be done by determining whether the determined magnitude of the perfusion signal deviates below a benchmark (e.g. an expected value or range), modifying the oscillation period of the heart rate signal used to determine the magnitude of the perfusion signal, and determining a new magnitude of the perfusion signal. ICDs and other sensing devices may experience problems with oversensing in relation to the heart rate signal. In some sensing devices, after a sensed R wave is detected, there is a short blanking period when further electrical activity is not sensed, then a period of automatic gain control whilst sensitivity returns to a baseline before the next R wave. However, electrical signals that are sensed after the blanking period, in the automatic gain control period, may be included in the heart rate calculations, i.e. are incorrectly sensed as R waves, and therefore incorrectly raise the measured heart rate. This could occur if the QRS is broad, for example for a bundle branch block patient, or if the T waves are very prominent and are therefore detected as R-waves (leading to a measured heart rate value of double the actual heart rate value). This means that the measured heart rate may be higher than the actual heart rate, meaning that an incorrect, low perfusion value may be returned, prompting an unnecessary shock to be given. For example, if the heart rate determined from the heart rate signal is incorrectly measured as twice the actual rate, then half of the segments of the perfusion signal will comprise just a trough part, and half will comprise just the peak part. When combined, these will cancel, and an artificially low perfusion value is determined.

To mitigate this effect, the device may be configured to determine whether the determined perfusion value is low (e.g. is below a threshold value, for example more than 2 or 3 percent less than the acceptable value). If it is determined that the perfusion value is low, the original perfusion signal is then segmented again using a heart rate signal (e.g. an electrogram (EGM)) for which some of the presumptive R waves are omitted. This may be done by excluding alternate R waves, or by calculating the intervals between groups of sensed R waves, looking for clusters of similar R-R intervals and then selecting the R waves that fit to this cluster of R-R intervals for example. A new perfusion value is then determined. Alternatively, the original heart rate signal may be re-analysed to detect the heart rate, using a different gain or different blanking window, i.e. the original R-wave detection algorithm can be modified, and a new perfusion value returned.

If the new perfusion value is within an acceptable range, then a shock is avoided. If not, the shock is then given. This step allows the device to check if an alternative interpretation of the heart rate shows electro-mechanical synchrony. If the alternative heart rate is correct, an acceptable perfusion value is returned if the patient is well and no shock is given. If the patient is unwell, the perfusion value will be low with any heart rate, therefore it is appropriate for the device to give a shock.

Figure 5:
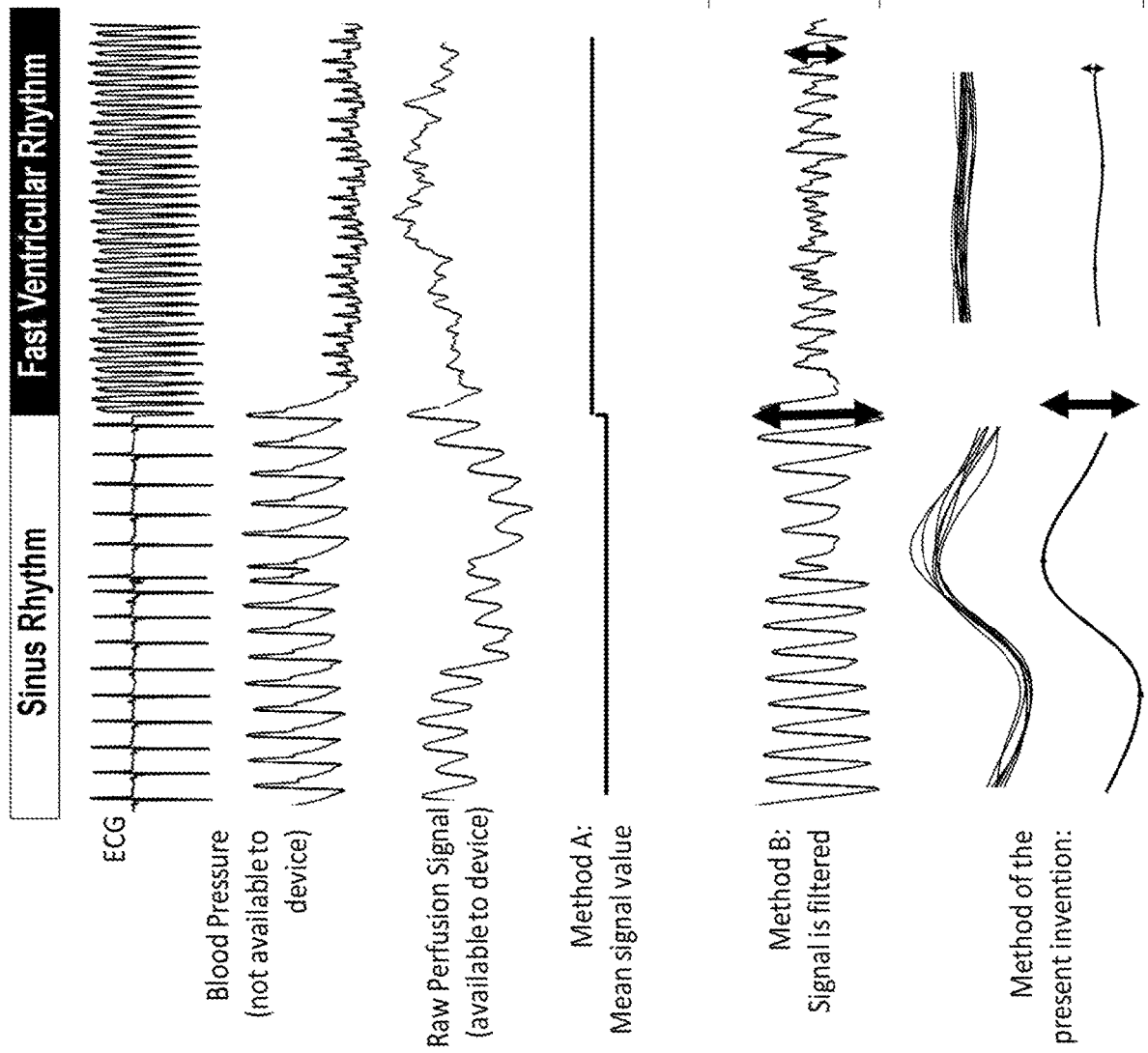
FIG. 5 is an example comparing perfusion signal processing according to different methods.
Figure 6:
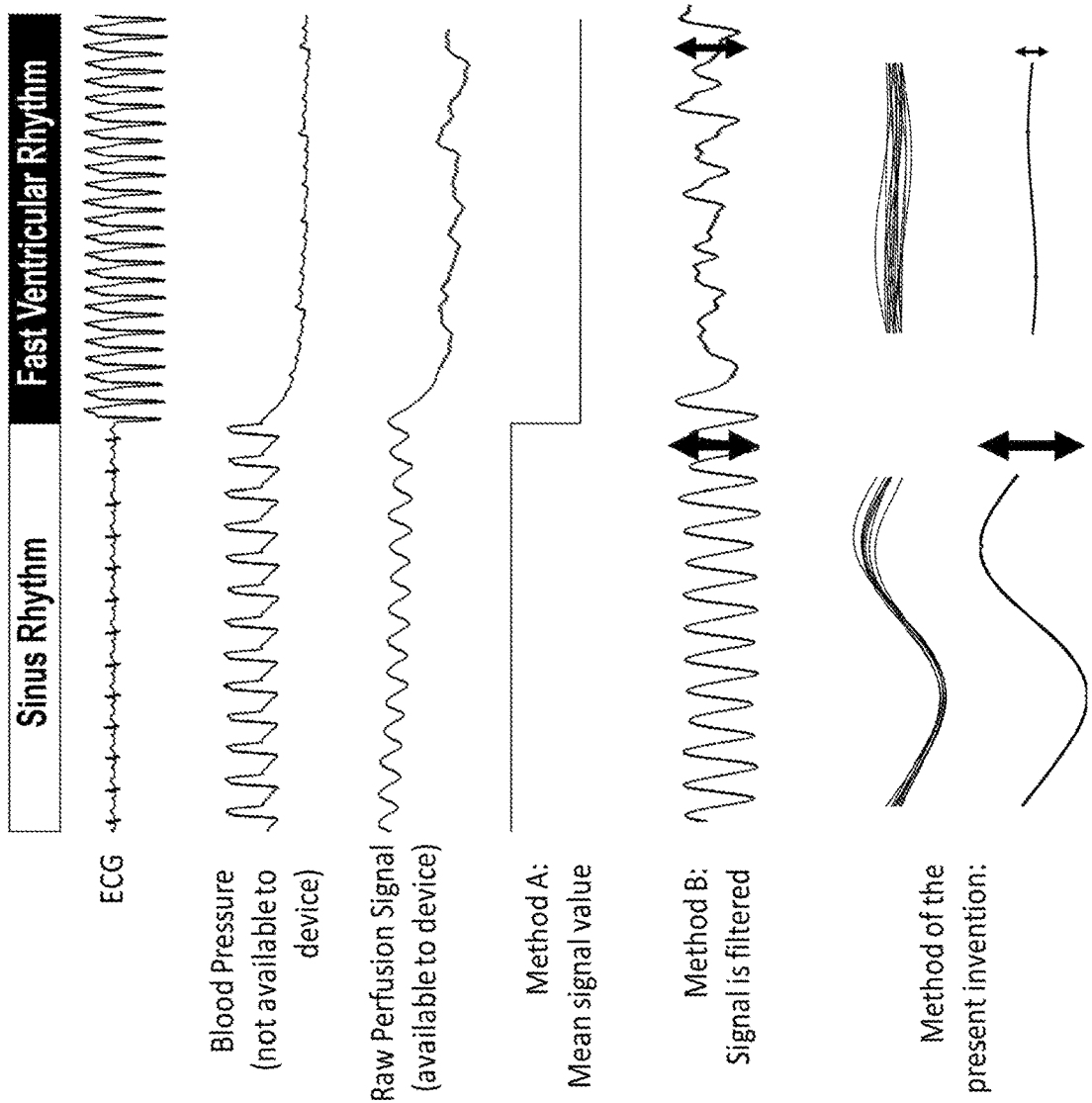
FIG. 6 is another example comparing perfusion signal processing according to different methods.

It was mentioned earlier that prior art methods of perfusion signal processing methods may sometimes provide an inaccurate representation of the true hemodynamic state of the individual. FIGS. 5 and 6 illustrate the differences between the known methods of perfusion signal processing and the perfusion signal processing according to the present invention.

FIG. 6 illustrates an exemplary case where an individual goes into VT and the blood pressure reduces significantly. Unlike the blood pressure signal, it can be seen that the perfusion signal is much noisier than the blood pressure signal. The first method (method A) compared against the method according to the present invention uses a mean absolute value of the perfusion signal. In this case, similarly to the significant drop of the blood pressure, there is also a significant drop in the general absolute values of the perfusion signal, the use of calculating a mean absolute value of the perfusion signal does indicate an appropriate fall in the absolute mean value over certain amount of time period. However, the perfusion signal needs to be monitored over a relatively long period in order to detect such a fall in the mean value, and to account for random fluctuations over time in the local perfusion signal. This is to say, the method relies on data from preceding intervals and bases the interpretation of local perfusion data on an assessment of its absolute magnitude over time. This requires extended periods of acquisition of perfusion data and increases energy consumption of the controller. Furthermore, even with more perfusion data acquired over a longer periods than that of the present invention, the decrease in the perfusion signal (and hence the hemodynamic state) is not as clear as when calculated according to the present invention. When the method of the present invention is used, most of the noisy signals during fast ventricular rhythm are disregarded, as these signals simply do not oscillate according to the oscillation of the ECG. Therefore, most of the noise signals are canceled out, and the result is the significant contrast of the perfusion signal oscillation magnitude during sinus rhythm and fast ventricular rhythm. The second method (method B) compared against the method according to the present invention uses band pass filtering of the perfusion signal. In this case, the filtering method is unsuccessful and is unable to remove the oscillation that was in fact due to noise. This method is particularly weak where the noise component is in the form of a fluctuation with some oscillatory behavior, as it is difficult to distinguish such noise signal from a true perfusion signal which also pulses. As such, the amplitude of the oscillation due to noise is still calculated and hence the significant decrease in the perfusion signal is not reflected in the values representing hemodynamic state found using the second method. As noted previously, even the noisy signals that occur with some oscillatory behavior are disregarded when the present method is used, because these noise signals do not line up with the ECG oscillations.

FIG. 5 illustrates an exemplary case where the individual goes into VT and the blood pressure falls greatly. In this case, however, the absolute perfusion signal values actually rise despite the fact that the blood pressure drops and the relative perfusion signal magnitude also drops in comparison to when in sinus rhythm (which may occur due to small shifts in sensor position or orientation). As in the case illustrated with reference to FIG. 6, the first method (method A) using the absolute mean value and the second method (method B) using band pass filter are compared against the method according to the present invention. Due to the increase in the absolute values of the perfusion signal, the absolute mean value of the perfusion signal is calculated as having increased. Therefore the first method fails to detect the blood pressure fall and hence fails to determine the true hemodynamic state of the individual. The second method again does indicate some fall but not one which is as significant as the one found using the present invention. The oscillations due to noise signal have not been removed using the bandpass filter, such that the fall is detected but the severity of the situation is not represented as clearly in the hemodynamic values output from the method. The perfusion signal processing method according to the present invention calculates the amplitude of the noise fluctuation as being very low in this case also.

As can be seen above, the perfusion signal processing according to the present invention outputs reliable values even in cases where other methods may fail to output reliable values indicating the true hemodynamic state of the individual.

As such, it can be seen that even after filtering, removal of artefacts, or noise suppression, quantifying based on an absolute magnitude or magnitude in respect to a reference state may result in an inaccurate representation of the hemodynamic state of the individual. In contrast, when the perfusion signal is processed according to the present invention, perfusion signal can be quantified to represent a true hemodynamic state even in the presence of noise and artefact by utilizing the relationship between the cyclical oscillations in the tissue perfusion signal and the cyclical electrical activity of the heart.

As illustrated above, in the method according to the present invention it is not necessary to obtain data over a long period of time, which is required for other methods. Therefore, it is not necessary for large amounts of memory or power to be provided in order to store data over a protracted period. In one embodiment, a history of data during an episode of cardiac arrhythmia or for a series of different episodes of cardiac arrhythmia may be stored in memory for future analysis or comparison against current data. Furthermore, as the perfusion signal processing of the present invention is done mainly in the time domain (whilst filtering in the frequency domain is used for improved accuracy, the main inventive concept lies in processing in the time domain), the perfusion signal data may be collected only over a short period of time, for example based on the charge time of the device so as to maximise the available data before a decision for therapy to be delivered. In other cases, the time may be varied to be based on a fixed number of cardiac cycles, or be based on an assessment of the consistency or quality of the derived signal. Furthermore, as the method is more robust to changes in sensor position and other fluctuations; the need to have data from immediately before the suspected arrhythmia is lessened as new value may be compared to a previously calculated results. In any case, the processing power requirement for the signal processing according to the present invention is significantly lower than those relying only on the frequency filtering.

When the therapy guide decision maker receives a reliable quantified value obtained from the perfusion signal which represents the hemodynamic state of an individual as described above, the value is determined as either high or low. The criteria for differentiating whether the value is high or low is based upon a predetermined threshold value. In other embodiments, the predetermined threshold value may be customizable or dynamic. This is to say, the threshold value may be based upon a database of values representing hemodynamic state during other electrical and hemodynamic circumstances of the individual, or other individuals. For example, the threshold value may be based on previous values obtained during the individual's routine activities, or determined during situations simulating the pathological states such as rapid ventricular pacing or induction of VT testing. The threshold value may also be selected based upon hemodynamic state values obtained during previous time periods and selected as a multiple/fraction of the values. For example, if in a particular patient during normal rhythm the range of values representing hemodynamic state are between 5 and 20, and in that particular patient VT (either spontaneously arising or mimicked using rapid ventricular pacing) produces a value of 2, then a suitable threshold to program might be 3 for tachycardias detected. When a tachycardia is detected the value of the hemodynamic state and would be evaluated. If it were below 3 the device would proceed to provide therapy (for example, overdrive pacing or defibrillation). In this example, if the value of the hemodynamic state was instead much higher, at 7 or 8, the device may not provide therapy. Preferably, the device is pre-programmed with a threshold for therapy with the option of adjusting the threshold in light of clinical experience in that patient, or in light of newer developed modules for measuring hemodynamic status.

Figure 7:
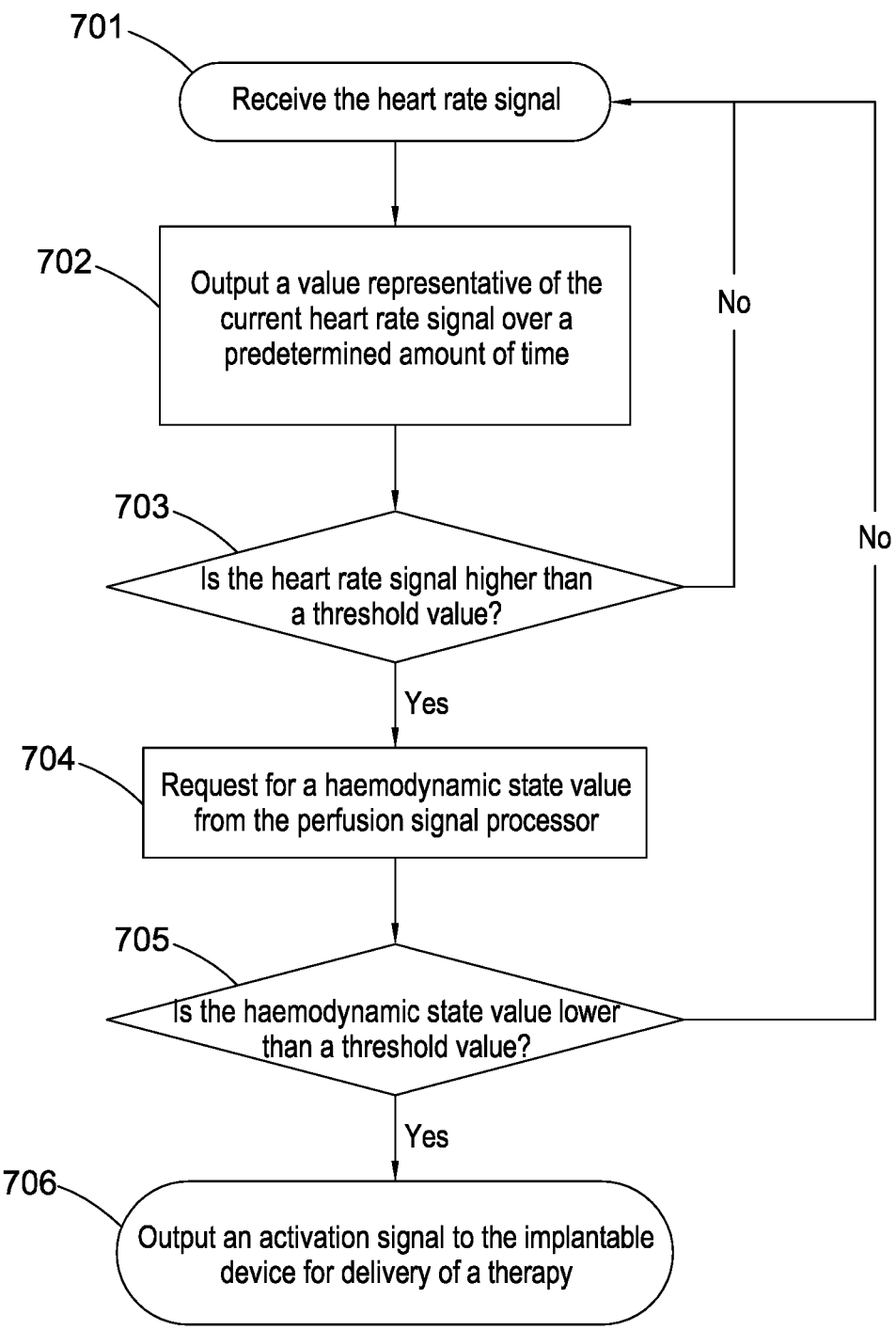
FIG. 7 is a flow diagram illustrating the algorithm used by a therapy guide decision maker according to an embodiment of the present invention.

Referring back to FIG. 2, it can be seen that the therapy guide decision maker of an embodiment according to the present invention is configured to receive cardiac electrical signal. As such, the cardiac electrical signal may be used to determine the condition of the individual initially, and the hemodynamic state value may be used in conjunction with the cardiac electrical signal to ensure: prevention of inappropriate therapies that may be caused by various the ECG signal errors; delay/prevent delivery of a therapy by the implantable or externally wearable device in case of hemodynamic stable cardiac rhythmic malfunction; and check whether the delivery of therapy by the implantable or externally wearable device has been successful. The algorithms used by the therapy guide decision maker of an embodiment according to the present invention are illustrated as a flow diagram in FIG. 7, showing steps 701, 702, 703, 704, 705 and 706. The therapy guide decision maker is configured to output a signal, which activates the implantable or externally wearable device to deliver a therapy, to the implantable or externally wearable device according to the outcome of the algorithm.

In the algorithm, in order to reduce the risk of delivering therapy inappropriately in circumstances where the patients are in a normal heart rhythm but there is an error in the ECG signal received, the device requests information from the hemodynamic sensor once a ventricular arrhythmia has been diagnosed using the ECG signal. This involves determining whether the ECG signal value obtained is higher or lower than a threshold value/range. Such condition depends on the implantable or externally wearable device. For example, in the case where the implantable device is an ICD, it is determined that the individual is having a VF where the ECG signal value is higher than a threshold value.

In an embodiment where the implantable or externally wearable device is a defibrillator, the activation signal from the device causes the defibrillator to deliver Anti-Tachycardia Pacing or a shock to treat the heart rhythm disturbance.

In another embodiment where the implantable or externally wearable device is a nerve stimulator, the activation signal from the device causes the nerve stimulator to deliver pulsation or deactivate pulsations which stimulate a branch of the autonomic nervous system to increase blood pressure through vasoconstriction.

In yet another embodiment where the implantable device is a pacemaker, the activation signal from the device causes the pacemaker to increase its pacing rate to prevent pre-syncope or syncope.

In another embodiment in which the implantable device is a pacemaker, the device, rather than using the ventricular lead which is either sensing true VF or electrical noise mimicking VF the device, should utilize the electrical activity from an atrial pacemaker lead or if present left ventricular pacemaker lead (in CRT devices) or His lead, to segment the tissue perfusion data and its further calculation as described above. If the individual is in a normal rhythm then the atrial electrical activity will be concordant with the tissue perfusion oscillations and the device interprets this as malfunction of the ventricular lead/sensor. If the individual is in ventricular fibrillation, as the potential random oscillations in the tissue perfusion signals will not line up with either the organized or disorganized atrial signals, this will then be interpreted as the patient is in VF and as such therapy will be initiated.

In some cases, leads or sensors for obtaining the cardiac electrical signal may be damaged and acquire a signal which is mixed with electrical noise that are indistinguishable from the actual cardiac electrical signal which represents the individual's cardiac activities. In such cases information extracted from the noise mixed signal may not validly represent the individual's actual condition. As such, it cannot be reliably determined whether a therapy should be delivered by the implantable or externally wearable device or not. The implantable or externally wearable device could regularly or continuously request data on the hemodynamic state using electrical information from other leads. By doing this, it is possible to regularly check for any errors that maybe occurring in the ECG signals, as well as monitoring the individual's condition.

After the delivery of therapy the implantable or externally wearable device may request further data on the hemodynamic state to confirm improvement. The device may then utilize this information to confirm the successful interpretation of the pre-therapy data and/or therapy delivery.

In summary, tissue perfusion signals obtained from a variety of methods including laser Doppler, spectroscopy, ultrasound Doppler are interpreted with reference to the electrical activity from the heart to isolate the amplitude of cyclical oscillations in tissue perfusion that correspond to the cyclical electrical activation of the heart. The resultant value representing the hemodynamic state is interpreted with reference to predetermined or customized criteria to differentiate hemodynamic states. Whilst the example embodiment discussed in the specific description includes an ICD, it will be clear to the skilled person that the hemodynamic states information can be used by any other implantable or externally wearable device for treating cardiac arrhythmia such as a pacemaker or a nerve stimulator to guide therapy delivery. The addition of this information on hemodynamic status to ICD or external defibrillator algorithms deciding therapy delivery is particularly advantageous as it would be expected to reduce the number of shocks an ICD or external defibrillator device needs to deliver during a time when a high rate of electrical signals is observed. This high rate could be due to ventricular tachycardia or due to noise. Electrical dysrhythmias and would also allow the assessment of the impact of therapies aimed at reducing the detrimental impact of VT on cardiac output. The skilled person will appreciate that the use of hemodynamic state reliably extracted by a controller according to the present invention may also be particularly advantageous when used in conjunction with any implantable or externally wearable devices for treating cardiac arrhythmia.

By using the perfusion signal processing as described above, it will be appreciated by the skilled person that it is possible to obtain are liable value representative of the true hemodynamic status. Therefore, using this value, it is possible for the therapy guide decision maker to determine whether a therapy should be delivered by the implantable or externally wearable device or not in a more reliable manner.

The control device of the present invention may be incorporated into any existing cardiac therapy guide modules. For example, it could be integrated with an implantable or externally wearable device, or be integrated with a hemodynamic state monitor or a perfusion signal sensor so that the sensor can output a value representing a hemodynamic state from the perfusion signal data obtained from the sensor itself.

Whilst many of the example embodiments above are described in relation to implantable or externally wearable cardiac devices, the device of the present invention may be incorporated into various other devices. In fact, the device of the present invention may be incorporated into any system which uses perfusion signal to determine a hemodynamic state of an individual.

In one embodiment, the device of the present invention may be adapted to monitoring local hemodynamic state and outputting the determined hemodynamic state for the user to view on a display. Such local hemodynamic state displayed is used for patients in whom there is concern about the degree of perfusion in different parts of the body. For example, an operation may involve moving a flap of tissue, connected to the circulation by just one artery. Over the next few hours and days after the operation, it is necessary to re-operate if the connection fails such that the tissue loses blood supply. Currently known methods for monitoring whether the connection (blood supply to the tissue) is lost involves a laser Doppler perfusion monitor which displays the trace of the perfusion signal as a graph, or a mean value representing the perfusion signal collected over a predetermined period of time. This would then be monitored by the user wherein it can be determined that the connection has failed if there is a drop in the graph or the value output. As discussed in detail above, raw perfusion signal is very noisy and currently known devices require for continuous human input for determining whether the connection is lost or not. By implementing a device according to the present invention for determining a hemodynamic state of the perfusion signal acquired, it is possible to obtain a much more reliable value which represents the actual hemodynamic state of the patient.

Furthermore, as the values representing the hemodynamic state are more reliable, it is possible to implement an algorithm which outputs a signal to alert the user when the hemodynamic state value decreases below a threshold value. As such, the device may simply display the hemodynamic state values obtained from the perfusion signal according to the present invention, or output a signal to notify the user when the hemodynamic state falls below a predetermined threshold value. In the latter case, the algorithm used is similar to when the device is connected to an implantable or externally wearable cardiac device, but it alerts the user rather than to activate an implantable or externally wearable cardiac device. In this embodiment, local hemodynamic state values are determined by using a number of different sensors in different parts of the body. Each perfusion signal acquired from each sensor is processed separately, by dividing each signal into frames in accordance with an oscillation period of the heart rate signal then combining at least two frames of the same signal, such that a hemodynamic state value is obtained for each perfusion signal. Due to the perfusion signal processing method of the present invention, a graph of the hemodynamic state values obtained or the mean value output is more reliable than those output by the known devices.

In an embodiment, the device of the present invention is configured to output a signal to control the implantable or externally wearable device based on the determined magnitude of the perfusion signal. The device may be configured to output a signal to modify the settings of the implantable or externally wearable device, for example to optimise the AV (atrioventricular) and/or VV (ventriculo-ventricular) delays of pacemakers and/or Cardiac Resynchronisation Therapy (CRT) devices based on the determined magnitude of the perfusion signal. A method of optimising the AV (atrioventricular) and/or VV (ventriculo-ventricular) delays is described in WO 2006/008535, which is hereby incorporated by reference.

For example, a range of device settings may be applied (e.g. an AV delay of 40, 80, 120, 160, 200 ms). At each setting, the magnitude of the perfusion signal is determined. The setting that gave the highest perfusion value would then be selected and a control signal sent to the device to select this setting. Alternatively, a graph of AV delay against perfusion value may be plotted, a curve fitted, and the setting corresponding to the highest point on the curve selected. VV delays settings may be varied from −50 ms to +50 ms for example and optimised in the same manner. All pacemakers can have AV optimisation, CRT devices can also have VV optimisation.

The device may therefore be adapted for optimization of pacemaker settings. The normal settings of a pacemaker can be changed for patients, for example those with heart failure and those using Cardiac Resynchronisation Therapy pacemaker devices. These settings may be changed and the hemodynamic results measured by a hemodynamic sensor, which may measure the perfusion signal. A perfusion value may then be determined as has been described herein and used to determine the optimal setting.

In an embodiment, the determined magnitude of the perfusion signal can thus be used to determine the settings of the pacemaker, for example to determine the optimal settings for the delay between the atria and the ventricles or between the two ventricles. This could be done with an implanted device at regular intervals or using an external device for example. As has been described previously, the device may be integrated with the pacemaker, or separate. For example, an external perfusion signal sensor may be used on a patient with an existing implantable device to make a series of measurements in one session, change the settings of the implantable device in accordance with the perfusion values determined from the settings, and send the patient away. Alternatively, the sensor is integrated with the implantable device, or implanted or wearable, and the device can continuously make measurements as it tests the settings whilst the patient is at home, without intervention from the doctor.

Although the above methods and devices have been described in relation to a perfusion signal, a signal which is a measure of the volume of blood in the thoracic cavity can be used in place of the perfusion signal. For example, a lead impedance signal, which is a continuously generated measure of the impedance of the leads of an implantable device such as a ICD or a pacemaker and the portion of the heart tissue and thoracic cavity between the leads is a measure of the volume of blood in the thoracic cavity. A lead impedance signal varies with the heart beat on a beat by beat basis, reflecting the volume of blood within the assessed cardiac chamber. Pacemakers and ICDs which are known in the art are configured to intermittently measure the lead impedance. A continuous measurement of the lead impedance can be made in a similar manner. The signal which is a measure of the volume of blood in the thoracic cavity may be analysed in the same manner described above in relation to the perfusion signal.

While certain embodiments have been described, these embodiments have been presented by way of example only, and are not intended to limit the scope of the inventions. Indeed the novel methods and apparatus described herein may be embodied in a variety of other forms; furthermore, various omissions, substitutions and changes in the form of methods and apparatus described herein may be made without departing from the spirit of the inventions. The accompanying claims and their equivalents are intended to cover such forms of modifications as would fall within the scope and spirit of the inventions.

The invention claimed is:

1. A control system comprising:
   a first sensor, configured to measure a first signal which is a perfusion signal of an individual or a signal which is a measure of a volume of blood in the thoracic cavity of the individual;
   a second sensor, configured to measure a signal representative of the heart rate of the individual;
   a controller configured to:
   receive the first signal and the signal representative of the heart rate of the individual;
   extract a plurality of frames from the first signal, wherein each extracted frame of plurality of extracted frames having an extracted frame length, which is a time period determined from an oscillation cycle from the signal representative of the heart rate of the individual which is simultaneous with the frame, the plurality of frames corresponding to consecutive segments of the first signal, wherein extracting the plurality of frames further comprises correcting for a difference in phase between the signal representative of the heart rate of the individual and the first signal;
   adjust the plurality of frames to have a single frame length; and
   determine a magnitude of the first signal from at least two frames of the plurality of frames, wherein the controller is configured to combine the at least two frames of the plurality of frames having the frame length which is the first time period determined from the oscillation period of the signal representative of the heart rate of the individual, and wherein the magnitude of the first signal is found by taking an amplitude of the combined first signal; and
   a device for hemodynamic intervention, wherein the controller is configured to output a signal to the device for hemodynamic intervention based on the signal representative of the heart rate of the individual and a comparison of the magnitude of the first signal with a threshold.

2. The system according to claim 1, configured to standardize the first signal prior to combining the at least two frames of the plurality of frames.

3. The system according to claim 1, wherein the oscillation cycle is an R-R interval.

4. The system according to claim 3, wherein correcting for any difference in phase between the signal representative of the heart rate of the individual and the first signal comprises extracting each frame such that the beginning of the frame is located at a time point on the perfusion signal corresponding to the location of the corresponding R-wave plus a fixed interval.

5. The system according to claim 1, wherein the device is configured to receive a multiple number of first signals from a number of sensors and determine a magnitude of each first signal from at least two frames of a plurality of frames extracted from the same first signal.

6. The system according to claim 5, configured to associate the first signals with a concurrently received signal representative of the heart rate of the individual.

7. The control system according to claim 1, wherein the controller is configured to output a signal to activate the device for hemodynamic intervention when a magnitude of the signal representative of the heart rate of the individual is above a first threshold value and a magnitude of the first signal is below a second threshold value.

8. The system according to claim 1, wherein the device for hemodynamic intervention is an implantable device or an externally wearable device.

9. The system according to claim 1, wherein the device for hemodynamic intervention is a defibrillator.

10. The system according to claim 9, wherein multiple frames are extracted from the first signal over a predetermined time period, wherein the predetermined time period is a charge time of the device.

11. The device according to claim 1, wherein the first signal is a lead impedance signal.

12. The device according to claim 1, wherein the first sensor is a perfusion sensor and the second sensor is a heart electrical activity sensor.

13. The device according to claim 1, wherein the controller is further configured to confirm that there is a single significant peak and a single trough in the combined first signal.

14. The device according to claim 13, wherein if more than one significant peak or more than one trough is detected, the controller is further configured to discard the combined first signal.

15. A method comprising:
    receiving a first signal, which is a perfusion signal of an individual or a signal which is a measure of a volume of blood in the thoracic cavity of the individual;
    receiving a signal representative of the heart rate of the individual; extracting a plurality of frames from the first signal, each extracted frame of the plurality of extracted frames having an extracted frame length, which is a time period determined from an oscillation cycle from of the signal representative of the heart rate of the individual which is simultaneous with the frame, the plurality of frames corresponding to consecutive segments of the first signal, wherein extracting the plurality of frames further comprises correcting for a difference in phase between the signal representative of the heart rate of the individual and the first signal;
    adjusting the plurality of frames to have a single frame length;
    determining a magnitude of the first signal from at least two frames of the plurality of frames, wherein the at least two frames of the plurality of frames having the frame length which is the first time period determined from the oscillation period of the signal representative of the heart rate of the individual are combined, wherein the magnitude of the first signal is found by taking an amplitude of the combined first signal; and
    outputting a signal to a device for hemodynamic intervention based on the signal representative of the heart rate of the individual and a comparison of the magnitude of the first signal with a threshold.

16. The method according to claim 15, wherein the first signal is standardized prior to combining the at least two frames of the plurality of frames.

17. The method according to claim 15, wherein the oscillation cycle is an R-R interval.

18. The method according to claim 15, wherein a multiple number of first signals are received from multiple sensors and a magnitude of each first signal from at least two frames of a plurality of frames extracted from the same first signal is found.

19. The method according to claim 18, wherein the first signals are associated with a concurrently received signal representative of the heart rate of the individual.

20. A computer storage medium comprising code for execution by a processor, the code, when executed by the processor causing the processor to perform the method according to claim 15.

\* \* \* \* \*